Figure 1:
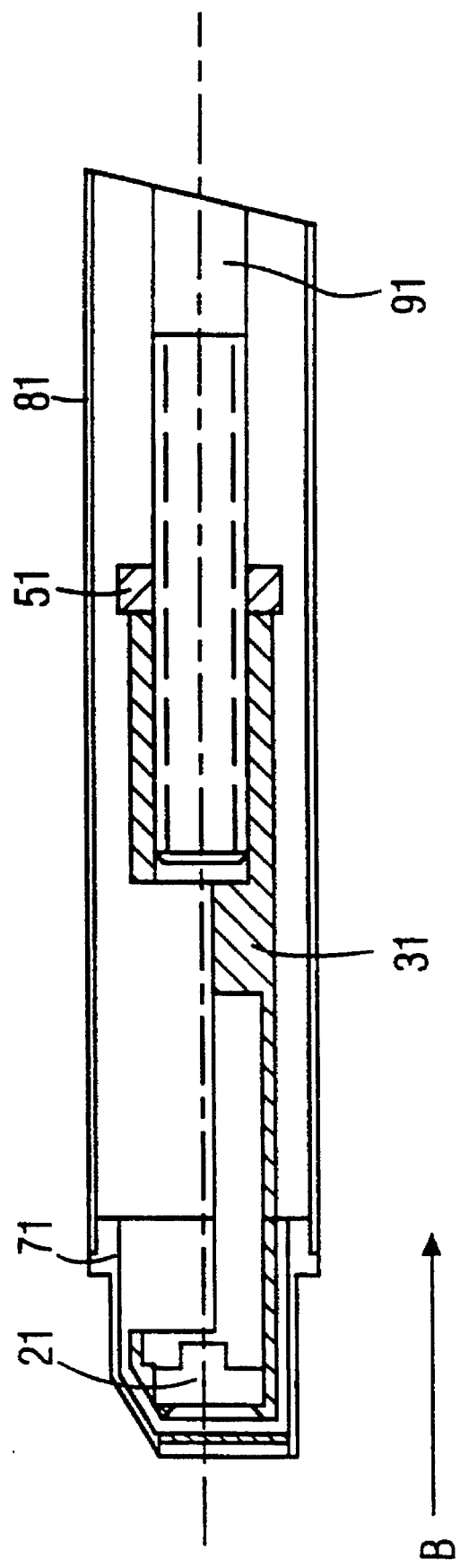

United States Patent [19]
Gallagher

[11] Patent Number: 5,488,832
[45] Date of Patent: Feb. 6, 1996

[54] MATCHED THERMAL EXPANSION SUPPORT SYSTEM

[75] Inventor: Brian W. Gallagher, Highland Lakes, N.J.

[73] Assignee: Philips Electronics North America Corporation, New York, N.Y.

[21] Appl. No.: 259,947

[22] Filed: Jun. 15, 1994

[51] Int. Cl.[6] ................................................. F25B 19/00
[52] U.S. Cl. ........................................... 62/51.1; 250/352
[58] Field of Search .............................. 62/51.1; 250/352

[56] References Cited

U.S. PATENT DOCUMENTS 5,235,817  8/1993  Gallagher et al. ...................... 62/51.1
5,274,237  12/1993  Gallagher et al. .................. 250/370.15

*Primary Examiner*—Ronald C. Capossela
*Attorney, Agent, or Firm*—Paul R. Miller

[57] ABSTRACT

A matched thermal expansion support system for cryogenically cooled x-ray spectrometers is described for the purpose of holding x-ray detecting crystals precisely in position throughout large temperature changes. This thermal matching is achieved by a detector holder, having an axial thermal movement characteristic, mounted on a support having an equal, but opposite, thermal movement characteristic.

3 Claims, 2 Drawing Sheets

MATCHED THERMAL EXPANSION SUPPORT SYSTEM

The present invention is directed to support systems for use in cryogenically cooled spectrometers forming x-ray spectra, more particularly, the present invention involves such support systems providing matched thermal expansion characteristics.

BACKGROUND OF THE INVENTION

Cryogenic cooling apparatus for cooling radiation detectors to cryogenic temperatures are well known and widely used in x-ray spectrometry and electron microscopy. In such spectrometers x-rays are detected from a specimen being spectrometrically examined, and radiation from the specimen is detected by a cryogenically cooled detector to convert the radiation to electrical signals in a known way for spectroscopic analysis.

Such detectors involve elongated structures known in the art as cold fingers. Such a cold finger is cantilevered from a Dewar arrangement so as to place a detector within the region of an electron beam of a microscope, for example, adjacent to the specimen. The interior of the electron microscope and the region surrounding the cold finger are within an evacuated chamber, and cooling of the detector is accomplished by the cold finger being thermally conductively connected to a source of cryogenic cooling, such as the Dewar containing liquid nitrogen.

Such structures may be seen by way of previous patents U.S. Pat. Nos. 5,235,817 and 5,274,237 of which the present inventor is a common inventor and which patents are assigned to the same assignee as the present application. In these previous prior art cryogenically cooled arrangements, the radiation detector is supported at the end of a cantilevered cold finger and maintained in the vicinity of the specimen. Because of thermal contraction occurring when the detecting unit is cooled, the radiation detector is subjected to movement on the cold finger support. Such movement caused by temperature changes at temperatures, such as 77° K., the temperature of liquid nitrogen, for example, results in movement of the detector crystal of about 0.040 to 0.060 inches. Such movement of the detector crystal significantly decreases the performance and sensitivity of the detector crystal.

Current practice according to the prior art fixes the cold finger at an interface between a detector cap and a specimen housing. This allows between 0.040 and 0.060 inches of detector crystal movement as the cold finger shrinks.

SUMMARY OF THE INVENTION

The presently claimed invention is directed to a support mounting structure for maintaining the radiation detector in cryogenically cooled structures, such as electron microscopes and x-ray spectrometers, with substantially improved position maintenance of the detector during operation.

The presently claimed invention involves a structure in which a detector holder for holding a detection crystal and a support for supporting the detector holder are each made of respective materials having equal and opposite thermal shrinkage. That is, the construction of the detector crystal support is of a different material than that of the detector crystal holder such that material shrinkage for the detector holder is equal in magnitude, but opposite in direction to that of the support so that the affect of temperature and thermal movement is cancelled out.

Consequently, the presently claimed invention provides a detector holder structure for holding a radiation detecting crystal with the detector holder structure being of a first material having a first temperature shrinkage characteristic, and a support arrangement for supporting the detector holder in the cryogenic system with the support arrangement being of a second material having a second temperature shrinkage characteristic which is equal and opposite to that of the first temperature shrinkage characteristic of the first material for the detector holder structure. Thermal movement of the detecting crystal is then prevented or at least substantially prevented.

The presently claimed invention enables the maintenance of the detector crystal position throughout a wide temperature range, such as from about 300° K. to about 77° K. Moreover, any type of detector where the detector location is important and must be maintained in position although being subject to large temperature changes can be used in this arrangement.

Consequently, a matched thermal expansion support system for apparatus, such as a cryogenically cooled detector system, which may be used in x-ray spectrometers or electron microscopes, is provided. A typical use of the present invention is in the cryogenically cooled detection of electron microscope specimens in which a detector such as a silicon-lithium, or SiLi, detector is utilized. Such matched thermal expansion support systems according to the present invention provide significant advantages and improvements for performance and sensitivity of detection units over a wide temperature variation.

BRIEF DESCRIPTION OF THE DRAWING FIGURES

The structure of the invention may be seen by reference to the drawing figures which show in:

FIG. 1 an example of the prior art system; and

Figure 2:
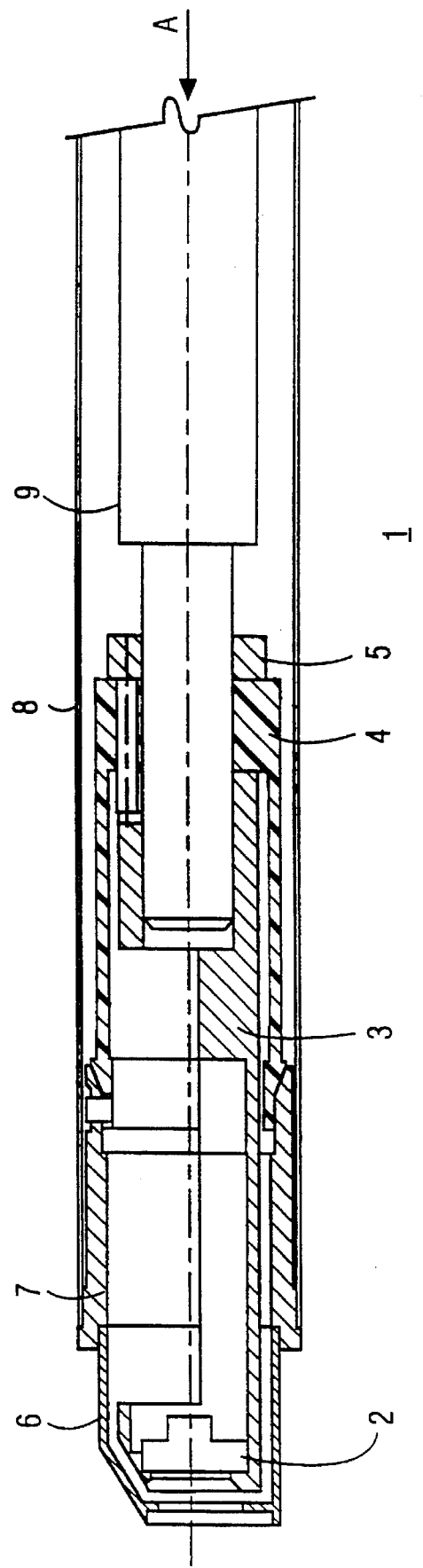

FIG. 2 an arrangement of a matched thermal expansion support system according to the present invention.

DESCRIPTION OF THE INVENTION

Current practice, according to the prior art, fixes a radiation detector with a radiation detector crystal 21 at the end of a cantilevered cold finger 91 as shown in FIG. 1. The cold finger 91 and detector crystal 21 are maintained within a tubular member 81, and an insert 71 closes the end of the tubular member to maintain a detecting unit vacuum. The detector crystal 21 is attached to the cold finger 91 by a metal detector holder 31 which is fixed on the cold finger by way of a jam nut 51.

During operation of a cryogenically cooled structure, the radiation detector crystal 21 is subject to thermal shrinkage in the direction B because of the wide range of temperatures used. Such thermal shrinkage of the detector crystal may be in the range of 0.040 and 0.060 inches and causes distortion of measurements of x-rays from sample specimens, such as made, for example, in the apparatus of U.S. Pat. Nos. 5,235,817 and 5,274,237.

The matched thermal expansion support system 1 shown in FIG. 2 of the present application is constructed with a detector crystal 2, such as a silicon-lithium detector used in electron microscope detectors, which detector is held by a detector holder 3 of a metal, such as aluminum. This detector holder 3 is then held by a tubular structure 4 made of a material such as Kel-F. The material Kel-F is a fluorocarbon plastic which is commercially available as a polychlorotrifluoroethylene or PCTFE which is both a thermal and electrical insulator. This tubular structure 4 is fixed onto the end of a copper cold finger 9 in the cryogenic structure by way of a brass jam nut 5. The entire arrangement is maintained within a stainless steel tube 8 which is fixed to an aluminum cap 6 surrounding the detector crystal 2. The aluminum cap 6 is epoxied to a stainless steel insert 7 which is welded to the end of the stainless steel tube 8.

This tubular arrangement of the stainless steel tube 8 having the tubular stainless steel insert 7 surrounds the radiation detector crystal 2 held by the detector holder 3 and Kel-F support 4 connected against the detector holder 3 to maintain the detector crystal 2 in the vicinity of a specimen being irradiated by x-rays or electron beams. The detection of x-rays given off from the specimen occurs by the detector crystal 2. Electrical connections (not shown) are then made to appropriate hardware for determination of specimens.

The entire structure of the support system is maintained at the end of the cold finger 9 on which an axial force is provided from a spring (not shown) of a cryogenic structure in the direction A, as may be seen in FIG. 2. This maintains the detector in the direction toward the specimen.

Such an arrangement according to the present invention enables the maintenance of the detector crystal in its position throughout a wide temperature range. The temperature can range from a liquid nitrogen ambient to about room temperature, i.e., over a range of at least some 220° C., i.e., 300° K. to about 77°. Because of the mounting of the detector crystal 2 on the detector holder 3 of the present invention with the detector holder 3 being in an abutting arrangement with the Kel-F support 4, then thermal expansion or shrinkage of the detector holder will be in an axial direction, for example, while the thermal expansion or shrinkage of the Kel-F support will be in an opposite axial direction.

Thus, the thermal characteristics of the structure and materials of the detector holder and the support are matched, and shrinkage, for example, is equal in magnitude, but opposite in direction so that any changes of position of the detector crystal caused by temperature shrinkage or expansion are cancelled. This results in an significant improvement of the performance and sensitivity for the detecting unit.

What I claim:

1. A structure for use in cryogenic coolers comprising a detector holder for holding a detector and a support for supporting the detector holder, each of said detector holder and said support being made of respective different-materials having equal and opposite movement due to temperature.

2. A detecting arrangement for use in cryogenic measurement devices comprising (a) detector holder means for holding a radiation detecting crystal, said detector holding means being a first material having a first temperature movement characteristic, and (b) support means for supporting said detector holder means in a system having a wide temperature range, said support means being of a second material having a second temperature movement characteristic, said detector holder means and said support means being arranged so that temperature changes in said system result in equal and opposite thermal movement of the detector holder means and support mean, thereby preventing any thermal movement of the detecting crystal.

3. A detecting arrangement according to claim 2, wherein said first and second temperature movement characteristics are temperature shrinkage of said first and second materials.

\* \* \* \* \*